United States Patent
Jayaswal et al.

(10) Patent No.: US 10,463,597 B2
(45) Date of Patent: Nov. 5, 2019

(54) PERSONAL CARE COMPOSITION

(71) Applicant: Conopco, Inc., Englewood Cliffs, NJ (US)

(72) Inventors: Amit Jayaswal, Bihar (IN); Zhengrong Li, Shanghai (CN); Yingying Pi, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 111 days.

(21) Appl. No.: 14/401,376

(22) PCT Filed: Apr. 28, 2013

(86) PCT No.: PCT/EP2013/058779
§ 371 (c)(1),
(2) Date: Nov. 14, 2014

(87) PCT Pub. No.: WO2013/174615
PCT Pub. Date: Nov. 28, 2013

(65) Prior Publication Data
US 2015/0110728 A1 Apr. 23, 2015

(30) Foreign Application Priority Data

May 22, 2012 (WO) ............... PCT/CN2012/075888
Jul. 24, 2012 (EP) ................................... 12177585

(51) Int. Cl.
*A61K 8/81* (2006.01)
*A61K 8/34* (2006.01)
*A61K 8/42* (2006.01)
*A61Q 5/02* (2006.01)
*A61Q 19/10* (2006.01)
*A61K 8/73* (2006.01)
*A61Q 5/00* (2006.01)

(52) U.S. Cl.
CPC .............. *A61K 8/8158* (2013.01); *A61K 8/34* (2013.01); *A61K 8/347* (2013.01); *A61K 8/42* (2013.01); *A61K 8/737* (2013.01); *A61Q 5/00* (2013.01); *A61Q 5/006* (2013.01); *A61Q 5/02* (2013.01); *A61Q 19/10* (2013.01); *A61K 2800/244* (2013.01)

(58) Field of Classification Search
CPC combination set(s) only.
See application file for complete search history.

(56) References Cited

U.S. PATENT DOCUMENTS

| | | | |
|---|---|---|---|
| 5,194,639 A | 3/1993 | Connor | |
| 5,853,709 A | 12/1998 | Willis et al. | |
| 6,495,498 B2 * | 12/2002 | Niemiec | A61K 8/731 424/401 |
| 7,414,152 B2 * | 8/2008 | Galopin | A61K 8/42 558/414 |
| 2002/0077256 A1 | 6/2002 | Niemiec et al. | |
| 2003/0176303 A1 | 9/2003 | Niemiec et al. | |
| 2004/0157755 A1 | 8/2004 | Niemiec et al. | |
| 2006/0210508 A1 | 9/2006 | Gamez-Garcia | |
| 2008/0096786 A1 | 4/2008 | Holt et al. | |
| 2009/0130040 A1 | 5/2009 | Jonchiere | |
| 2011/0002868 A1 | 1/2011 | Bierganns et al. | |
| 2012/0015894 A1 * | 1/2012 | Terada | A61K 8/362 514/26 |
| 2012/0263659 A1 | 10/2012 | Subkowski et al. | |
| 2013/0053295 A1 * | 2/2013 | Kinoshita | A61K 8/463 510/427 |
| 2013/0323388 A1 * | 12/2013 | Talsma | A61K 8/34 426/533 |

FOREIGN PATENT DOCUMENTS

| | | | |
|---|---|---|---|
| CN | 101904908 | 12/2010 | |
| EP | 1080714 | 3/2001 | |
| EP | 1529515 | 5/2005 | |
| FR | 2752730 A1 * | 3/1998 | ............... A61K 8/34 |
| FR | 2920975 | 3/2009 | |
| JP | 6107527 | 4/1994 | |
| JP | 2001002535 | 1/2001 | |
| JP | 2008521860 | 6/2008 | |
| JP | 2008189582 | 8/2008 | |
| WO | WO9206154 | 4/1992 | |
| WO | WO9825581 | 6/1998 | |
| WO | WO2006058755 | 6/2006 | |
| WO | WO2011003068 | 1/2011 | |
| WO | WO2012110387 | 8/2012 | |

OTHER PUBLICATIONS

Search Report in PCTEP2012068350, dated Dec. 21, 2012.
Written Opinion in PCTEP2012068350, dated Dec. 21, 2012.
GNPD, Deep Action Shampoo, Deep Action Shampoo, Oct. 2, 2009, 1-2.
IPRP in PCTEP2013058779, dated Aug. 18, 2014.
Search Report in EP12177585, dated Dec. 18, 2012.
Search Report in PCTEP2013058779, dated Nov. 18, 2013.
Written Opinion in EP12177585, dated Dec. 18, 2012.
Written Opinion in PCTEP20132013058779, dated May 19, 2014.
Deep Action Shampoo, Mintel GNPD, Oct. 2009, pp. 1-3 (Record ID# 1189857—same as Record ID#12018480.

* cited by examiner

Primary Examiner — John Pak
Assistant Examiner — Nathan W Schlientz
(74) Attorney, Agent, or Firm — Greenberg Traurig, LLP

(57) ABSTRACT

Disclosed is a personal care composition comprising cooling active and copolymer comprising acrylamidopropyltrimonium chloride, wherein the weight ratio of the amount of the cooling active to the amount of the copolymer is in the range from 1:5 to 100:1. The copolymer improves deposition of the cooling active during topical application of the product to skin.

10 Claims, No Drawings

PERSONAL CARE COMPOSITION

TECHNICAL FIELD OF THE INVENTION

The present invention relates to an improved personal care composition comprising a cooling active. In particular the present invention relates to such compositions and which comprise a copolymer comprising acrylamidopropyltrimonium chloride. The present invention also relates to the use of such a composition and/or copolymer for improving deposition of cooling actives, especially during topical application to the skin.

BACKGROUND TO THE INVENTION

Cooling actives, such as menthol and the like, have been used in personal care formulations to provide a variety of benefits. Besides the largely cosmetic benefits of fresh sensation and/or scent left on skin after topical use, cooling actives may also have local anaesthetic and counterirritant qualities.

Unfortunately, however, cooling actives may be difficult to formulate at high concentration in personal care formulations and/or there may be safety and environmental constraints on their use at levels high enough to produce a noticeable effect on topical application.

Thus the present inventors have recognised a need to improve the efficiency of deposition of cooling actives from personal care formulations to address one or more of these issues. To this end the present inventors have found that, compared with conventional deposition polymers such as cationic guar, certain copolymers can enhance deposition of cooling actives. In particular, the present inventors have found that copolymers comprising acrylamidopropyltrimonium chloride are especially efficacious.

One such copolymer is the acrylamidopropyltrimonium chloride/acrylamide copolymer commercially available from Ashland as N-Hance SP-100®, wherein the same has been described for use in delivering actives such as silicone, emollients and antimicrobial agents such as zinc and selenium onto hair and skin by forming coacervates with anionic surfactants. Such copolymers are also described, for example, in WO 2011/003068 A1 (HERCULES INC.). However, we have now found that copolymer comprising acrylamidopropyltrimonium chloride can improve the delivery of cooling actives and that such delivery can be effective even where the copolymer is not employed in great excess compared with the amount of cooling active.

SUMMARY OF THE INVENTION

In a first aspect, the present invention is directed to a personal care composition comprising cooling active and copolymer comprising acrylamidopropyltrimonium chloride, wherein the weight ratio of the amount of the cooling active to the amount of the copolymer is in the range from 1:5 to 100:1.

In another aspect, the present invention provides a method for providing a cooling sensation to the skin of an individual comprising the step of topically applying the composition of the first aspect to at least a portion of the skin of the individual.

In a still further aspect, the present invention provides use of a copolymer comprising acrylamidopropyltrimonium chloride for improving deposition of a cooling active.

All other aspects of the present invention will more readily become apparent upon considering the detailed description and examples which follow.

DETAILED DESCRIPTION

Except in the examples, or where otherwise explicitly indicated, all numbers in this description indicating amounts of material or conditions of reaction, physical properties of materials and/or use may optionally be understood as modified by the word "about".

All amounts are by weight of the final personal care composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

The composition of the present invention comprises cooling active. Cooling actives are substances which have a physiological cooling effect, particularly on the skin. A large number of cooling actives of natural or synthetic origin have been described. The most well-known is menthol, particularly l-menthol, although others may be mentioned including menthone, isopulegol, N-ethyl p-menthanecarboxamide ("WS-3"), N,2,3-trimethyl-2-isopropylbutanamide ("WS-23"), ethyl 2-(p-menthane-3-carboxamido) acetate ("WS-5"), N-(4-menthoxyphenyl)-p-menthane-3-carboxamide ("WS-12"), menthyl lactate (Frescolat® ML), menthone glycerine acetal (Frescolat® MGA), mono-menthyl succinate (Physcool®), mono-menthyl glutarate, O-menthyl glycerine (CoolAct® 10), menthyl-N,N-dimethylsuccinamate, 2-sec-butylcyclohexanone (Freskomenthe®), and N-(4-cyanomethylphenyl)-p-menthanecarboxamide (Evercool® 180). These compounds may be employed as the cooling active in the present invention, either individually or in mixtures of two or more.

Menthol is the most preferred cooling active owing to its wide availability and consumer acceptability. Therefore it is preferred that the cooling active comprises menthol, more preferably the cooling active comprises at least 50% menthol by total weight of the cooling active, more preferably still at least 60% and most preferably from 80 to 100%.

Another especially preferred cooling active is N-(4-cyanomethylphenyl)-p-menthanecarboxamide which is commercially available from Givaudan under the name Evercool® 180 and which is said to have a long-lasting cooling effect. Therefore it is preferred that the cooling active comprises N-(4-cyanomethylphenyl)-p-menthanecarboxamide.

The N-(4-cyanomethylphenyl)-p-menthanecarboxamide may be used in place of menthol or as a replacement of a part thereof. In particularly preferred embodiment the cooling active comprises menthol and N-(4-cyanomethylphenyl)-p-menthanecarboxamide. The N-(4-cyanomethylphenyl)-p- menthanecarboxamide may be used in relatively small amounts and still enhance the cooling effects of menthol. Thus it is preferred that the cooling active comprises menthol and N-(4-cyanomethylphenyl)-p-menthanecarboxamide in a weight ratio of menthol to N-(4-cyanomethylphenyl)-p-menthanecarboxamide of at least 1:1, more preferably at least 2:1 and most preferably from 3:1 to 10:1.

The exact amount of cooling active to be employed in the compositions of the invention will depend, amongst other things, on the intended use of the composition and the cooling power of the active. Typically, however, the personal care composition comprises the cooling active in an amount of from 0.001 to 2% by weight, more preferably from 0.01 to 1.5%, more preferably still from 0.1 to 1% and most preferably from 0.2 to 0.7%.

The composition of the present invention comprises a copolymer comprising acrylamidopropyltrimonium chloride. Suitable copolymers include the synthetic polyelectrolytes described, for example, in WO 2011/003068 A1 the disclosure of which is hereby incorporated by reference in its entirety but especially paragraphs [00039] to thereof. Thus the copolymer preferably has a charge density from about 0.001 to 4 meq g$^{-1}$, more preferably 1.0-3.0 meq g$^{-1}$, more preferably still 1.0-2.5 meq g$^{-1}$ and most preferably 1.5-2.2 meq g$^{-1}$. The copolymer preferably has a molecular weight (Mw determined by size exclusion chromatography) in the range 500,000 to 2 million g mol$^{-1}$, more preferably 800,000 to 1.5 million. Preferably, the copolymer comprises acrylamide in addition to the acrylamidopropyltrimonium chloride, more preferably the copolymer has the INCI Name: Acrylamidopropyl Trimonium Chloride/Acrylamide Copolymer.

An especially suitable copolymer is commercially available from Ashland as N-Hance SP-100®. N-Hance SP-100® has a Mw in the range of from 1 to 1.2 million g mol$^{-1}$ and a charge density in the range of from 1.5 to 2.0 meq g$^{-1}$.

The copolymer is unexpectedly found to enhance deposition of cooling active even when present in relatively low amounts compared with the amount of cooling active. Thus the composition of the invention has the weight ratio of the amount of the cooling active to the amount of the copolymer in the range from 1:5 to 100:1. Preferably, the weight ratio of the amount of the cooling active to the amount of the copolymer is in the range of from 1:2 to 20:1 or even in the range of from 1:1 to 10:1. Furthermore at high ratios of copolymer to cooling active the copolymer may bring unwanted sensory properties to the personal care composition (e.g. "stringiness") which may detract from the enhanced sensory properties provided by the cooling active. In addition high amounts of copolymer may destabilise the composition in some cases, especially where the composition comprises other active agents (such as for example, conditioning active and/or antidandruff agent) which may be prematurely flocculated by the polymer.

The amount of copolymer in the composition depends therefore to some extent on the amount of cooling active. Typically, however, the personal care composition comprises the copolymer in an amount of from 0.001 to 1% by weight of the composition, more preferably from 0.01 to 0.7% and most preferably from 0.05 to 0.4%.

In addition to the copolymer, it is preferred that the composition also comprises a cationic deposition polymer other than the copolymer, which may also assists in deposition of cooling active and/or other active ingredients in the composition.

Suitable cationic deposition polymers may be a homopolymer or be formed from two or more types of monomers. The weight-average molecular weight of the polymer will generally be between 5 000 and 10 000 000 unified atomic mass units, typically at least 10 000 and preferably from 100 000 to 2 000 000. The polymer will have cationic nitrogen containing groups such as quaternary ammonium or protonated amino groups, or a mixture thereof.

Preferably, the cationic deposition polymer is cationic polysaccharide. Such cationic polysaccharide includes for example, cationic celluloses and hydroxyethylcellulose, cationic starches and hydroxyalkyl starches, cationic polymer based on guar gum. More preferably the cationic deposition polymer is (or comprises) cationic polygalactomannan, especially guar or cassia derived polygalactomannan modified with hydroxypropyl trimonium chloride.

Specific non-limiting examples of cationic guar polymer includes Jaguar® C-14S, Jaguar® C-13S, Jaguar® C-17, Jaguar® C-500, Jaguar® C-162, Jaguar® Excel.

It is highly preferred that compositions according to the invention should contain from 0.01% to 2% wt. of the composition cationic deposition polymer in addition to the copolymer, more preferably from 0.05 to 0.5% wt. and most preferably from 0.08 to 0.25% by weight of the composition.

Additionally or alternatively the weight ratio of the amount of the cationic deposition polymer to the amount of the copolymer is preferably in the range from 10:1 to 1:10, more preferably from 5:1 to 1:5, most preferably 2:1 to 1:2.

The personal care composition of the invention may be in any form but is preferably suitable for topical application to the skin either as a leave-on or rinse-off composition. However, the copolymer is found to assist deposition of the cooling active to produce a cooling effect which remains even after rinsing and therefore the present invention may be particularly advantageous for providing cleansing compositions.

Thus in a preferred embodiment the composition comprises cleansing surfactant.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic surfactants are the alkyl sulfates and alkyl ether sulfates. These materials have the respective formulae $R_{20}SO_3M$ and $R_{10}(C_2H_4O)_xSO_3M$, wherein $R_2$ is alkyl or alkenyl of from 8 to 18 carbon atoms, x is an integer having a value of from about 1 to about 10, and M is a cation such as ammonium, alkanolamines, such as triethanolamine, monovalent metals, such as sodium and potassium, and polyvalent metal cations, such as magnesium, and calcium. Most preferably $R_2$ has 12 to 14 carbon atoms, in a linear rather than branched chain.

Preferred anionic cleansing surfactants are selected from sodium lauryl sulphate and sodium lauryl ether sulphate(n) EO, (where n is from 1 to 3); more preferably sodium lauryl ether sulphate(n)EO, (where n is from 1 to 3); most preferably sodium lauryl ether sulphate(n)EO where n=1.

Preferably the level of alkyl ether sulphate is from 0.5 wt % to 25 wt % of the total composition, more preferably from 3 wt % to 18 wt %, most preferably from 6 wt % to 15 wt % of the total composition.

The total amount of anionic cleansing surfactant in compositions of the invention generally ranges from 0.5 wt % to 45 wt %, more preferably from 1.5 wt % to 20 wt %.

Compositions of the invention may contain non-ionic surfactant. Most preferably non-ionic surfactants are present in the range 0 to 5 wt %.

Nonionic surfactants that can be included in compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups. Alkyl ethoxylates are particularly preferred. Most preferred are alkyl ethoxylates having the formula R—(OCH$_2$CH$_2$)$_n$OH, where R is an alkyl chain of C12 to C15, and n is 5 to 9.

Other suitable nonionic surfactants include mono- or di-alkyl alkanolamides. Examples include coco mono- or di-ethanolamide and coco mono-isopropanolamide.

Further nonionic surfactants which can be included in compositions of the invention are the alkyl polyglycosides (APGs). Typically, APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_6$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92/06154 and U.S. Pat. No. 5,194,639, and the N-alkoxy polyhydroxy fatty acid amides, such as $C_{10}$-$C_{18}$ N-(3-methoxypropyl) glucamide.

Amphoteric or zwitterionic surfactant can be included in an amount ranging from 0.5 wt % to about 8 wt %, more preferably from 1 wt % to 4 wt % of the total composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

The composition of the invention preferably is suitable for providing a cooling sensation to the skin of an individual when topically applied thereto. In particular the present inventors have found that the compositions are especially suitable for cooling skin on the scalp.

Therefore it is preferred that composition is a hair care composition. The hair care composition according to the invention may be in any common product form used to treat hair. However, preferably, it is shampoo composition.

The hair care composition according to the invention may comprise any of the ingredients commonly found in hair treatment compositions depending on the product form. For example, where the composition is a shampoo it will comprise at least one cleansing surfactant such as is commonly employed in shampoos. Where it is a composition which aims to provide conditioning benefit, whether as part of a shampoo composition or a dedicated conditioning composition it will comprise a conditioning active. Suitable conditioning actives include fatty alcohols, silicones and cationic surfactants.

The present inventors have also recognised that the cooling sensation afforded by the hair care compositions of the invention may be advantageous in cuing delivery of actives from the composition. In particular the compositions of the present invention may be effective in enhancing the attractiveness of anti-dandruff compositions.

Thus in one embodiment the hair care composition comprises antidandruff agent. Antidandruff agents are compounds that are active against dandruff and are typically antimicrobial agents and preferably antifungal agents.

Antifungal agents typically display a minimum inhibitory concentration of about 50 mg/ml or less against *Malassezia* spp.

Suitable antidandruff agents include compounds selected from ketoconazole, climbazole, octopirox, metal pyrithione salts, and mixtures thereof.

The preferred azole based antifungal agents are ketoconazole and climbazole. Preferred metal pyrithione salts are zinc, copper, silver and zirconium pyrithione. The most preferred is zinc pyrithione.

Preferably, the antidandruff agent is present at from 0.01 to 5% wt. of the composition, more preferably from 0.1 to 2.5% wt. of the composition.

The invention will now be described with reference to the following non-limiting examples.

EXAMPLES

Example 1

Two shampoos were prepared, each containing 0.4 wt % menthol as cooling active. The Control shampoo contained 0.2 wt % of cationic modified polygalactomannan extracted from guar. The Test shampoo was identical to the Control shampoo but 50 wt % of the cationic guar was replaced with copolymer comprising acrylamidopropyltrimonium chloride (N-Hance® SP-100 ex. Ashland).

The deposition of menthol onto artificial skin by each shampoo was then determined as follows:
1. 0.5 g shampoo was mixed with 1.5 g water and used to wash artificial skin for 30 s by manual rubbing with a plastic stick, followed by removing the liquid;
2. A further 2 g of water was then used to wash the skin for 30 s, followed by removing the liquid;
3. The skin was then washed with 4 ml ethanol for 60 s to collect the deposited menthol.
4. The ethanol wash liquid was then filtered using a 0.45 μm filter before injection to GCMAS for quantification.
5. Five (5) replicas were done for each shampoo formulation.

The results are shown in Table 1.

TABLE 1

| Shampoo | Mean deposition ($\mu g/cm^2$) | Standard Deviation | 95% Conf. Interval |
|---|---|---|---|
| Control (0.2% Cationic Guar) | 3.29 | 0.53 | ±0.46 |
| Test (0.1% Cationic Guar + 0.1% acrylamidopropyltrimonium chloride/acrylamide) | 4.88 | 1.03 | ±0.90 |

The data shows that acrylamidopropyltrimonium chloride/acrylamide copolymer can significantly improve the deposition of cooling active.

Example 2

Two anti-dandruff shampoos were made by standard processes and had the formulations given in Table 2.

TABLE 2

| Ingredient % wt | Shampoo A | Shampoo 1 |
|---|---|---|
| Sodium Laureth Sulphate | 14 | 14 |
| Cocoamidopropyl betaine | 1.6 | 1.6 |
| Cationic Guar | 0.2 | 0.1 |
| acrylamidopropyltrimonium chloride/acrylamide copolymer* | — | 0.1 |
| Zinc Pyrithione | 1.0 | 1.0 |
| Menthol | 0.4 | 0.4 |
| Evercool ® 180** | — | 0.1 |
| Zinc sulphate | 0.1 | 0.1 |
| Dimethicone | 2.5 | 2.5 |
| Perfume | 0.75 | 0.75 |
| Sodium chloride | 0.6 | 0.6 |
| Acrylic Acid polymer (Carbomer) | 0.6 | 0.6 |
| Sodium Hydroxide | 0.3 | 0.3 |
| Preservative | 0.22 | 0.22 |
| Preservative | 0.009 | 0.009 |
| Water | To 100 | To 100 |

*N-Hance SP-100 ex. Ashland.
**Ex. Givaudan

The hair of 36 consumers was washed with both Shampoo A and Shampoo 1 (each Shampoo on half of the head) by expert hair washers. The consumers were then required to complete a questionnaire rating the performance of the two shampoos in both wet and dry stage.

At the 95% confidence level the following significant differences were observed:
Shampoo 1 gave more intense cooling immediately after wash, 30 minutes after wash and 1 to 2 hours after wash.
Shampoo 1 was cooler at the wet stage.
Shampoo 1 gave longer lasting cool feel in dry stage.

The invention claimed is:

1. A personal care composition, comprising:
cooling active;
cationic deposition polymer;
and
copolymer;
wherein the cooling active is in an amount of from 0.2 to 0.7% by weight;
wherein the copolymer is in an amount of from 0.01 to 0.4% by weight of the composition;
wherein the cationic deposition polymer is in an amount of from 0.05% to 0.5% by weight of the composition;
wherein the cooling active comprises menthol and N-(4-cyanomethylphenyl)-p-menthanecarboxamide in a weight ratio of 3:1 to 10:1;
wherein the copolymer is Acrylamidopropyl Trimonium Chloride/Acrylamide Copolymer;
wherein the weight ratio of the amount of the cationic deposition polymer to the amount of the copolymer is in the range from 2:1 to 1:2;
wherein the composition comprises a cleansing surfactant; and
wherein a weight ratio of the amount of the cooling active to the amount of the copolymer is in the range from 1:1 to 10:1.

2. The personal care composition as claimed in claim 1, wherein the cooling active comprises at least 50% menthol by total weight of the cooling active.

3. The personal care composition as claimed in claim 1, wherein the copolymer has a charge density from 1.0-3.0 meq $g^{-1}$.

4. The personal care composition as claimed in claim 1, wherein the composition comprises an anionic cleansing surfactant in a total amount of from 0.5 wt % to 45 wt %.

5. The personal care composition as claimed in claim 1, wherein the copolymer has a molecular weight in the range 500,000 to 2 million g $mol^{-1}$.

6. The personal care composition as claimed in claim 5, wherein the copolymer has a molecular weight in the range 800,000 to 1.5 million g $mol^{-1}$.

7. The personal care composition as claimed in claim 1, wherein the composition comprises the copolymer in an amount of from 0.05 to 0.4% by weight of the composition.

8. The personal care composition as claimed in claim 1, wherein the cationic deposition polymer comprises cationic polygalactomannan.

9. A method for providing a cooling sensation to the skin of an individual comprising the step of topically applying the composition of claim 1 to at least a portion of the skin of the individual.

10. The method as claimed in claim 9, wherein the portion of the skin is on the scalp of the individual.

* * * * *